US012730099B2

(12) United States Patent
Aigner et al.

(10) Patent No.: US 12,730,099 B2
(45) Date of Patent: Sep. 8, 2026

(54) SENSOR FOR DETERMINING THE CONCENTRATION OF AN ACIDIC OR BASIC COMPOUND AND USE OF A WATER-SOLUBLE PROTECTIVE LAYER HAVING pH BUFFERING PROPERTIES FOR PROTECTING THE SAME

(71) Applicant: EXIAS Innovative Diagnostics GmbH, Graz (AT)

(72) Inventors: Daniel Aigner, Graz (AT); Daniel Riechers, Hannover (DE); Xaver Gstrein, Graz (AT)

(73) Assignee: EXIAS INNOVATIVE DIAGNOSTICS GMBH, Graz (AT)

(*) Notice: Subject to any disclaimer, the term of this patent is extended or adjusted under 35 U.S.C. 154(b) by 296 days.

(21) Appl. No.: 18/423,021

(22) Filed: Jan. 25, 2024

(65) Prior Publication Data

US 2024/0310351 A1 Sep. 19, 2024

(30) Foreign Application Priority Data

Mar. 13, 2023 (EP) .................................... 23161573

(51) Int. Cl.
*G01N 33/18* (2006.01)

(52) U.S. Cl.
CPC ................................ *G01N 33/1886* (2013.01)

(58) Field of Classification Search
CPC .................................................. G01N 33/1886
(Continued)

(56) References Cited

U.S. PATENT DOCUMENTS 5,246,859 A 9/1993 Nelson et al.
5,496,521 A 3/1996 Leiner
(Continued)

FOREIGN PATENT DOCUMENTS

EP 0 873 517 B1 10/1998
EP 2 462 428 B1 6/2012
EP 3 789 760 A1 3/2021

OTHER PUBLICATIONS

UÃ§ar, Ahmet, et al. "pH-Activated Dissolvable Polymeric Coatings to Reduce Biofouling on Electrochemical Sensors." Journal of Functional Biomaterials 14.6 (2023): 329. (Year: 2023).*
(Continued)

*Primary Examiner* — Walter L Lindsay, Jr.
*Assistant Examiner* — Philip T Fadul
(74) *Attorney, Agent, or Firm* — Womble Bond Dickinson (US) LLP

(57) ABSTRACT

The present invention relates to a sensor for determining the concentration of an acidic or basic compound dissolved in water, wherein the determination is based on an ingress of gas or vapor of said compound, causing a change in pH value, within an inner buffer separated from a sample side by a membrane that is permeable to gases and impermeable to ions, characterized in that a layer is provided between the membrane and the sample side, wherein the layer substantially covers the membrane, wherein the layer is water-soluble and has pH buffering properties. The present invention further relates to the use of a water-soluble layer having pH buffering properties for protecting a sensor for determining the concentration of an acidic or basic compound from ingress of an acidic or basic gas during non-use of the sensor.

20 Claims, 1 Drawing Sheet

(58) Field of Classification Search
USPC .......................................................... 73/61.41
See application file for complete search history.

(56) References Cited

U.S. PATENT DOCUMENTS

| | | | | |
|---|---|---|---|---|
| 5,508,509 | A | 4/1996 | Yafuso et al. | |
| 6,200,444 | B1 | 3/2001 | Ahlers et al. | |
| 2007/0175769 | A1 * | 8/2007 | Hsiung .............. | G01N 27/4162<br>204/424 |
| 2012/0132813 | A1 | 5/2012 | Baumfalk et al. | |
| 2013/0270125 | A1 | 10/2013 | Lobber et al. | |

OTHER PUBLICATIONS

Extended European Search Report of EP 23 16 1573, Aug. 30, 2023, 5 pages.

Fritzsche, et. al., "Highly sensitive poisoning-resistant optical carbon dioxide sensors for environmental monitoring," Anal. Methods, 2017, vol. 9, pp. 55-65, The Royal Society of Chemistry 2017.

* cited by examiner

SENSOR FOR DETERMINING THE CONCENTRATION OF AN ACIDIC OR BASIC COMPOUND AND USE OF A WATER-SOLUBLE PROTECTIVE LAYER HAVING pH BUFFERING PROPERTIES FOR PROTECTING THE SAME

CROSS-REFERENCE TO RELATED APPLICATION

This application claims priority to European Patent Application No. 23 161 573.3 filed 13 Mar. 2023, the disclosure of which is hereby incorporated herein by reference.

FIELD OF THE DISCLOSURE

The present disclosure relates to a sensor for determining the concentration of an acidic or basic compound dissolved in water and to the use of a water-soluble protective layer having pH buffering properties for protecting such a sensor, in particular from ingress of another acidic or basic gas during non-use of the sensor.

BACKGROUND

It is common knowledge that $CO_2$ sensors based on detecting $CO_2$ due to its acidic properties, for instance those based on the Severinghaus principle, are negatively affected by other acidic or basic gases. If these gases enter the inner buffer of the sensor, they cause a change in the sensor response curve. For example, if the pka value of the penetrating acidic gas when dissolved is lower than that of carbon dioxide, this may lead to a reduction or complete loss of $CO_2$ sensitivity or—if the effect is at least partially reversible by outgassing of the acidic gas during operation—to a drift during the measurement.

The problem is relevant, in a similar manner, also for sensors for other acidic or basic gases (in the gas phase or dissolved) if their detection is based on their acidic or basic properties.

In the case of sensors for dissolved $CO_2$, the problem mainly concerns storage stability, since the absorption of acidic gases is a long-term process which does not occur during operation, when the sensor is in contact with the sample to be measured or aqueous operational or calibration solutions. Such solutions are buffered to some degree and are present almost throughout the whole operation time.

The problem is particularly relevant if the sensors cannot be stored under wet conditions between manufacturing and use. That is the case, for instance, when they are part of a multianalyte measurement system such as a measurement cell of a multiparameter analyzer and if other sensors in said system are not compatible with wet storage. That is the case for instance with some potentiometric sensors such as ion-selective electrodes (ISE) or some enzyme-based amperometric sensors for metabolites. In such systems, it is not possible to store the multianalyte measuring cells filled with buffered solution for the whole storage time (typically up to 12 months) without risking critical damage. This results in many additional boundary conditions for the design of such a measurement system, since components from which even small amounts of potentially harmful components are released (adhesives, plastics, resins which can release traces of acids/bases or components which can be transformed into those for example by oxidation) must be avoided as far as possible.

The problem is particularly pronounced with "wet optodes" (wet $CO_2$ optodes) having dispersed inner buffer particles, since the surface area is particularly large and the internal electrolyte volume and thus the buffer capacity are particularly low. However, a dispersed inner buffer is necessary to achieve a rapid sensor response and is also beneficial to mitigate problems arising from changes in the osmotic pressure in the inner buffer.

Previous attempts to cope with the problem in storage life of $CO_2$ sensors include the following:

U.S. Pat. No. 5,496,521 proposes to store the measuring cell filled with buffered solution, whereby undesirable osmotic effects, which are a known problem with completely closed Severinghaus sensors, are prevented by a connecting channel. However, the osmotic effects that are the focus of said patent are in any case a problem that does not concern the impairment of sensor stability by volatile acids/bases. Moreover, the wet storage as described in U.S. Pat. No. 5,496,521 is practically incompatible with the usual potentiometric ISE sensors or enzyme-based amperometric sensors for metabolites.

Fritzsche et. al. [Anal. Methods, 2017, 9, 55] have proposed to apply a cover layer made from a material exhibiting a comparatively high permeability to $CO_2$ while the permeability to gases causing damage to $CO_2$ optodes during storage (such as $H_2S$ or $NH_3$) is comparatively low. Even though that protective layer is investigated with non-Severinghaus based $CO_2$ optodes, which do not have a true inner buffer, the principle is supposed to be applicable to the Severinghaus sensors mentioned in this disclosure as well. However, such a layer can only provide temporary protection as it is based on slowing down the diffusion of potentially harmful gases. It also necessarily causes an adverse effect on sensor response time, as the diffusion of $CO_2$ is slowed down as well.

To increase stability during sterilisation, EP 3 789 760 A1 proposes the use of zinc carbonate, calcium carbonate or phosphates in the sensitive material of the sensor. These are components that are insoluble in common solvents and are part of the $CO_2$-sensitive particles. However, a limited neutralisation capacity is to be expected for these protective components ("scavengers") in the $CO_2$-sensitive particles, since the absorption capacity of the particles for these components is also limited. Furthermore, such inorganic salts often require a certain degree of wetting to unfold their scavenging properties, which means they may become ineffective under dry storage conditions. Thus, the need to control storage humidity may arise, resulting in storage conditions which are harder to control and may potentially interfere with the requirements of other parts of a measurement system. Alternatively, or in addition to this, such components can also be incorporated into cover membranes (sample-oriented, covering layers which, depending on their composition, can unfold a protective function for the underlying sensor layer). However, that increases the gas storage capacity of the $CO_2$ sensor and therefore leads to a slower response of the sensor as well as a stronger influence of measured values by the samples measured before ("memory effect"), without improving the buffer capacity of the sensor and thus its intrinsic robustness against storage effects.

In EP 2 462 428 B1, an optical sensor covered by a medium-facing, water-soluble layer is proposed, consisting of one or more sugar(s), inorganic salt(s), amino acid(s), glycerine, peptide(s), protein(s), or a combination thereof. The layer is designed to protect the sensor from harmful components released during radiation sterilization. Those harmful components can include free radicals or acidic compounds formed by reaction of those radicals with oxygen or water, therefore they are particularly harmful to $CO_2$ optodes such as those previously described, which are sensitive to acids. The ingress of those harmful compounds is prevented solely by the presence of a protective layer. Free radicals or acids are absorbed by that layer as they geometrically separated from the optical sensor by it.

EP 2 462 428 B1 focusses on reactors or vessels used in biotechnological applications, thus the protective layer must be made of a material which is not an issue if present in the culture medium once the reactor or vessel is used. On the other hand, the requirements on shape stability and specific absorption capacity for acidic or basic gases of the material are moderate. That contrasts with the focus of the present disclosure, which focusses on measurement cells of multiparameter analyzers. Because the measurement cell can be emptied in such a system, there is no need to use protective layer materials compatible with a certain (biological) medium, as long as the layer dissolves quickly and easily in water. Due to the typically very limited space in such measurement cells, the requirements on shape stability and specific pH buffer capacity of the protective layer are very high. It is also difficult to coat a thin and fully covering protective layer of a highly hydrophilic material onto the usual medium-contacting materials of sensors for dissolved gases (usually silicones or fluoropolymers).

Thus, there may still be a need for a sensor for determining the concentration of an acidic or basic compound, such as a $CO_2$ sensor, having improved storage stability, in particular in terms of preventing negative influences by (other) acidic or basic gases during storage.

OBJECT OF THE DISCLOSURE

The present disclosure aims at overcoming the problems and drawbacks described above. Thus, it may be a need to provide a sensor for determining the concentration of an acidic or basic compound, such as a $CO_2$ sensor, having improved storage stability, in particular in terms of preventing negative influences by acidic or basic gases during storage.

SUMMARY OF THE DISCLOSURE

The inventors have carried out diligent studies and have found that this object may be solved by covering a sensor membrane (where, upon use, gas from a sample side may enter an inner buffer of the sensor) on its exterior (sample-facing) side with a (protective) layer comprising or essentially consisting of a water-soluble bulk material and additionally comprising a substance having pH buffering properties (e.g. an organic or inorganic buffer salt). By taking this measure, acidic or basic gases from the environment may be trapped by the protective layer and thereby prevented from damaging the sensor by entering its inner buffer. That is of particular relevance in a setup where said sensor is a sensor for dissolved $CO_2$ and is part of a larger measurement system where a liquid sample is brought into a measurement cell which may additionally hold other sensors and said measurement cell is stored without being filled with an aqueous solution capable of providing at least some pH buffering between manufacturing and use for several weeks or months. Such a setup is typically present in analyzers capable of measuring several analytical parameters, as those parameters are measured by several individual sensors held together in only one measurement cell. Some sensor types are damaged if the measurement cell is filled with liquid before storage, for instance potentiometric ion sensors based on polymer membrane electrodes or enzyme-based amperometric sensors for metabolites. Both sensor types are very common in diagnostics analyzers. It is also common to bring together all sensors in a single measurement cell which is as small and simple as possible. A larger and more sophisticated measurement cell, allowing wet storage for only some sensors, would have negative effects on measurement time, required sample volume, complexity and manufacturing cost of the analyzer. Thus, all sensors in the measurement cell need to be compatible with a single storage condition (wet or dry).

In accordance with the present disclosure, said sensor is subjected to a buffered environment upon storage by covering it with a protective layer providing at least some buffer capacity. It is therefore protected against acidic or basic gases to at least some degree, without risking damage on additional sensors present in the measurement system (such as an analyzer used in diagnostics). The substances making up the protective layer has to be selected so that a maximum buffer capacity per volume is provided, since the volume is usually very limited in aforementioned measurement systems. Moreover, it is advantageous if the bulk component of the protective layer holds an adequate amount of bound water after drying under ambient conditions, without a particular drying procedure. If the water content in said "dry" state was too low, the buffer salt would at least partially crystallize, and the buffering effect of the protective layer could be compromised. If the water content was too high, the mechanical stability of the protective layer might be poor and there would be a risk of undesired water carry-over to other parts of the measurement system.

Furthermore, it is desirable for the protective layer to quickly and completely redissolve as soon as getting in contact with water during the startup of the multianalyte sensor system upon use.

Finally, the protective layer should be applicable to typical surface materials for gas sensors (silicones, fluoropolymers) in the form of an aqueous solution and its wetting ability on such materials should be good enough so a sensor (typically in the format of a round spot with a diameter of 1-5 mm) can be covered and remains covered also during evaporation of the water. If the wetting ability is not good enough, there is a high risk that the sensor spot will not be fully covered by the protective layer and its protective power will be poor.

Taking into account all aforementioned criteria, the material for the protective layer as well as its application protocol are chosen carefully. A thus protected sensor can be stored over an extended period of time. When the measuring cell holding the sensor is used, the protection layer is initially removed by rinsing with water within a short period of time and without any residues of the protective layer on the sensor membrane.

Accordingly, the present disclosure relates to a sensor (or sensor arrangement) for determining the concentration (amount, content) of an acidic or basic compound (i.e. for quantitatively determining an acidic or basic compound) dissolved in water, wherein the determination is based on an ingress of gas or vapor of said compound (into an inner buffer), causing a change in pH value within an inner buffer (substantially or completely) separated from a sample side by (means of) a (cover) membrane that is permeable to gases and impermeable to ions, characterized in that a (protective) layer is provided between the membrane and the sample side (in particular provided on the membrane and facing the sample side), wherein the layer substantially covers the membrane, wherein the layer is water-soluble and has pH buffering properties.

The present disclosure further relates to the use of a water-soluble (protective) layer having pH buffering properties for protecting a sensor (or sensor arrangement) for determining the concentration of an acidic or basic compound from ingress (entry) of an (another) acidic or basic gas during non-use (e.g. storage) of the sensor.

Other objects and many of the attendant advantages of embodiments of the present disclosure will be readily appreciated and become better understood by reference to the following detailed description of embodiments and the accompanying drawings.

DETAILED DESCRIPTION OF THE DISCLOSURE

Figure 1:
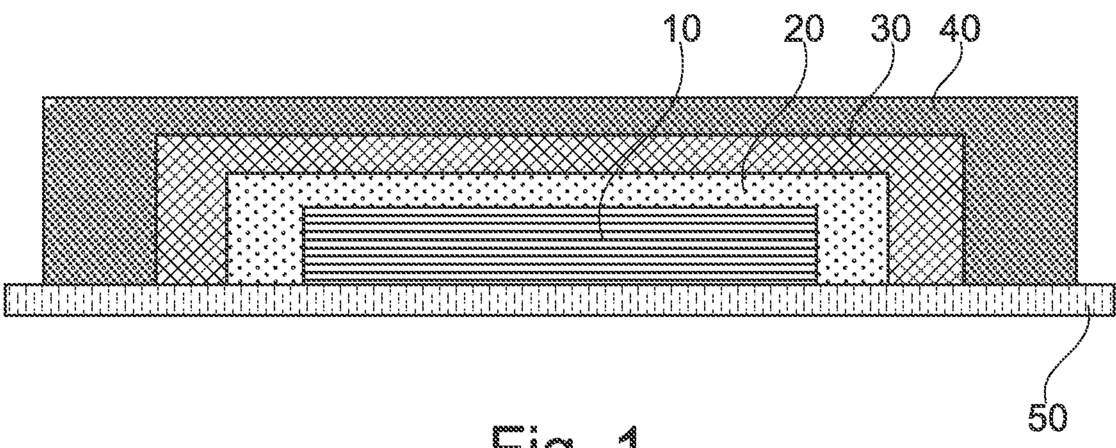
FIG. 1 schematically illustrates a sensor according to an embodiment.

Hereinafter, details of the present disclosure and other features and advantages thereof will be described. However, the present disclosure is not limited to the following specific descriptions, but they are rather for illustrative purposes only.

It should be noted that features described in connection with one exemplary embodiment or exemplary aspect may be combined with any other exemplary embodiment or exemplary aspect, in particular features described with any exemplary embodiment of a sensor may be combined with any other exemplary embodiment of a sensor and with any exemplary embodiment of a use and vice versa, unless specifically stated otherwise.

Where an indefinite or definite article is used when referring to a singular term, such as “a”, “an” or “the”, a plural of that term is also included and vice versa, unless specifically stated otherwise, whereas the word “one” or the number “1”, as used herein, typically means “just one” or “exactly one”.

The expression “comprising”, as used herein, includes not only the meaning of “comprising”, “including” or “containing”, but may also encompass “consisting essentially of” and “consisting of”.

In a first aspect, the present disclosure relates to a sensor, which may also be referred to as a sensor arrangement. The sensor is configured for determining the concentration of an acidic or basic compound, such as an acidic or basic gas, dissolved in water. Thus, the sensor is configured for quantitatively determining an acidic or basic compound.

In the context of the present application, the term “acidic compound” may in particular refer to a compound that leads to a pH value of less than 7 when dissolved in pure water. Analogously, the term “basic compound” may in particular refer to a compound that leads to a pH value of more than 7 when dissolved in pure water.

Suitable examples for the acidic compound include carbon dioxide ($CO_2$), sulfur dioxide ($SO_2$) and nitrogen oxides (NOx). Suitable examples for the basic compound include ammonia ($NH_3$), oximes and amines.

In an embodiment, the sensor is configured for determining the concentration of (dissolved) carbon dioxide. The determination of the concentration of carbon dioxide, for instance in blood and/or in respiratory air, is of particular relevance for medical reasons. However, it may be important to know the concentration of carbon dioxide in other applications as well, for example in the mining or in the food industry.

The determination of the concentration of an acidic or basic compound is based on a change in pH value in an inner buffer of the sensor. The inner buffer typically comprises or consists of micelles of a buffer solution or a dispersion of particles sensitive to acidic or basic compounds.

In an embodiment, the inner buffer contains a pH buffering compound, in particular in the form of a solution, such as dissolved in water. The pH buffering compound may in particular comprise a hydrogen carbonate (bicarbonate), such as sodium hydrogen carbonate, a phosphate, in particular a mixture of hydrogen phosphate and dihydrogen phosphate, such as disodium hydrogen phosphate and potassium dihydrogen phosphate, or an organic buffer salt.

In an embodiment, the inner buffer contains a dispersion of a (solid, particulate) pH buffering compound, in particular a hydrogen carbonate, such as sodium hydrogen carbonate, or an organic buffer salt in a liquid, in particular water, as disclosed for instance in EP 0 873 517 B1.

In an embodiment, the sensor further comprises at least one of a pH indicator and a pH electrode (i.e. a pH indicator and/or a pH electrode). For instance, a dye that changes an optical characteristic, such as its color, luminescence intensity, decay time or polarization axis, depending on the pH may be used as a pH indicator. Suitable examples of pH indicators are well known to a person skilled in the art. Additionally or alternatively, a pH electrode, in particular an ion-selective electrode or glass electrode, may be used for sensing changes in pH, typically in combination with a reference electrode. By taking these measures, any change in pH value caused by acidic or basic compound analytes that have entered the inner buffer can be determined.

The sensor further comprises a membrane, which may also be denoted as a cover membrane and which separates the inner buffer from a sample side.

In the context of the present application, the term “membrane” may in particular mean a flat structure (which may be planar as well as curved) which is at least partially permeable to one or more substances and is less permeable or even substantially impermeable to at least one other substance. A membrane can therefore also be described as a separation layer since it can separate substances from each other due to the different permeabilities. It may thus also be denoted as a selective barrier or a semipermeable membrane. The membrane in the context of the present application is in particular permeable to gases and (substantially) impermeable to ions.

In an embodiment, the membrane comprises, or is made from, silicone. The membrane may however also be made from any other material(s) suitable for allowing gases to pass through while retaining ions, such as buffer ions. Such other materials include, but are not limited to, amorphous fluoropolymers.

A layer is provided between the membrane and the sample side. In particular, the layer may be provided (directly) on (an exterior surface/side of) the membrane (and facing the sample side). The layer substantially (in particular completely) covers the membrane. Since the layer may protect the sensor from (undesired) acidic or basic gases, it may also be designated as protective layer.

In an embodiment, the protective layer has a thickness in a range of from 50 nm to 5 mm, in particular of from 500 nm to 1 mm, in particular of from 1 μm to 500 μm, in particular of from 5 μm to 100 μm.

The protective layer comprises (or consists of) a water-soluble (bulk) material and has pH buffering properties.

In the context of the present application, the term "water-soluble" may in particular mean that the bulk material of the protective layer can be easily dissolved with water. For instance, the water-soluble material may have a solubility in water at 20° C. of more than 20 g/l, in particular more than 40 g/l, in particular more than 100 g/l. Moreover, the water-soluble material may dissolve in water within less than 10 minutes, in particular within less than 5 minutes, in particular within 1 minute.

In the context of the present application, the term "protective layer" may in particular mean a material applied onto a sensor (typically onto its cover membrane) in the form of a solution, typically an aqueous solution, to form a wet film or droplet. Evaporation of the majority of water from the film or droplet yields the protective layer which essentially covers the sensor, remains hydrated to some degree and therefore is able to retain pH buffering properties.

In the context of the present application, the term "pH buffering properties" may in particular mean the characteristic of partially neutralizing acidic or basic compounds with less changes in pH value than without the pH buffering property.

In an embodiment, the protective layer comprises a polymer. In the context of the present application, the term "polymer" may particularly denote an organic compound having a (weight-average) molecular weight of at least 500 g/mol, in particular at least 1,000 g/mol, in particular at least 2,500 g/mol, in particular at least 5,000 g/mol, in particular at least 10,000 g/mol, and typically not more than 1,000,000 g/mol, such as not more than 500,000 g/mol. The polymer may include one or more types of repeating units, derived from respective monomers. Thus, the term "polymer" may also include a copolymer compound or a mixture of polymer and copolymer compounds. The polymer is not particularly limited as long as it can be easily dissolved in water. Moreover, the polymer itself may have pH buffering properties and/or should be suitable to reach a stable, partially hydrated state in which it can take up a pH buffering compound.

In an embodiment, the polymer is a hydrophilic polymer. In particular, the polymer may be selected from the group consisting of carboxymethyl cellulose, polyethylene glycol, polyvinyl alcohol and polyvinylpyrrolidone. For instance, carboxymethyl cellulose having a molecular weight of from 50 to 500 kDa, in particular 90 to 250 kDa, polyethylene glycol having a molecular weight of from 0.5 to 20 kDa, in particular 1 to 10 kDa, polyvinylpyrrolidone having a molecular weight of 0.3 kDa to 1.500 kDa, in particular 5 kDa to 40 kDa, or polyvinyl alcohol having a molecular weight of 3 kDa to 200 kDa and grade of hydrolysis of 80% to 100%, in particular 5 kDa to 30 kDa and grade of hydrolysis of 80% to 100% may be used. Carboxymethyl cellulose having a molecular weight of 90 kDa and polyethylene glycol having a molecular weight of 1 kDa have proven particularly suitable for forming a protective layer exhibiting an appropriate solubility behaviour.

In an embodiment, the layer comprises the polymer in an amount of from 10 to 99.5% by weight, in particular of from 40 to 98% by weight, in particular of from 50 to 95% by dry weight.

In an embodiment, the protective layer is applied in the form of an aqueous solution comprising the polymer in an amount of from 1 to 40% by weight, in particular of from 2.5 to 30% by weight, in particular of from 4 to 10% by weight.

In an embodiment, the polymer used as bulk material of the protective layer is selected to feature a water content when left to dry for 48 h under approximate environmental conditions of 25° C. and 50% RH of from 5 to 300% of the polymer weight, in particular of from 10 to 100% of the polymer weight, in particular of from 15 to 50% of the polymer weight.

In an embodiment, the water-soluble layer having pH buffering properties comprises a pH buffering compound. In particular, the pH buffering compound may be comprised in the layer in addition to the polymer. The pH buffering compound may be an inorganic compound (salt) or an organic buffer salt. The pH buffering compound comprised in the protective layer may be the same pH buffering compound as the pH buffering compound contained in the inner buffer or a different pH buffering compound.

In an embodiment, the pH buffering compound comprises an inorganic compound, in particular a hydrogen carbonate, such as sodium hydrogen carbonate. A hydrogen carbonate has proven particularly suitable for trapping (and neutralizing) any acidic or basic gases and thus buffering the pH value. In case of acidic gases, a hydrogen carbonate may release carbon dioxide. In case of basic gases, a hydrogen carbonate may convert to carbonate.

In an embodiment, the pH buffering compound comprises an organic buffer such as the "HEPPS" buffer, comprising a mixture of 4-(2-Hydroxyethyl)-1-piperazinepropanesulfonic acid and sodium hydroxide (molar ratio 2:1). It was found that using "HEPPS" instead of sodium bicarbonate, higher amounts of buffer salt can be present in the typical protective layer materials without crystallization of the buffer salt. Instead of the "HEPPS" buffer, other organic buffers can also be used, such as those based on 2-(N-morpholino) ethanesulfonic acid, 2,2',2"-Nitrilotriacetic acid, 2,2'-(Piperazine-1,4-diyl)di(ethane-1-sulfonic acid), N-(2-Acetamido)-2-aminoethanesulfonic acid, 2-Hydroxy-3-(morpholin-4-yl)propane-1-sulfonic acid, cholamine chloride hydrochloride, (3-(N-morpholino)propanesulfonic acid), (4-(2-hydroxyethyl)-1-piperazineethanesulfonic acid), 3-[[1,3-dihydroxy-2-(hydroxymethyl)propan-2-yl] amino]-2-hydroxypropane-1-sulfonic acid, {[1,3-Dihydroxy-2-(hydroxymethyl)propan-2-yl]amino}acetic acid, 2-Amino-2-(hydroxymethyl)propane-1,3-diol, 2-Aminoacetamide, (2-Aminoacetamido)acetic acid, [Bis(2-hydroxyethyl)amino]acetic acid, 3-{[1,3-Dihydroxy-2-(hydroxymethyl)propan-2-yl]amino}propane-1-sulfonic acid, N, N-Bis (2-hydroxyethyl)-2-aminoethanesulfonic acid, 2-{[1,3-Dihydroxy-2-(hydroxymethyl)propan-2-yl]amino}ethane-1-sulfonic acid, acetamidoglycine, 3-(N,N-Bis[2-hydroxyethyl]amino)-2-hydroxypropanesulfonic acid or Piperazine-1,4-bis(2-hydroxypropanesulfonic acid).

In an embodiment, the layer comprises the pH buffering compound in an amount of from 0.01 to 75% by weight, in particular of from 1 to 30% by weight, in particular of from 5 to 20% by weight.

In an embodiment, a ratio of the pH buffering compound with respect to the polymer used as bulk material of the layer is in a range of from 0.1 to 10 mmol (pH buffering compound)/g (polymer), in particular of from 0.25 to 5 mmol (pH buffering compound)/g (polymer), in particular of 0.5 to 2 mmol (pH buffering compound)/g (polymer). It is to be expected that a higher ratio of the pH buffering compound with respect to the polymer (i.e. a larger amount of pH buffering compound) is advantageous for preventing an ingress of another acidic or basic gas into the sensor, as long as crystallization of buffer salt does not occur.

In an embodiment, the water-soluble layer having pH buffering properties comprises a surfactant. By taking this measure, the applicability and/or wettability of the protective layer on different membrane surfaces may be improved. In particular, nonionic surfactants may be suitable for this purpose. Suitable examples thereof include polyoxyalkylene polyols, fatty alcohol polyglycol ether, polyalkylene glycolether and polyvinylpyrrolidone. In particular, polyoxyethylene (4) lauryl ether has proven particularly suitable for improving the applicability of the protective layer on different membrane surfaces.

In an embodiment, the layer comprises the surfactant in an amount of from 5 to 1000 ppm, in particular of from 20 to 250 ppm, in particular of from 25 to 100 ppm.

The manufacturing of the sensor, in particular the application of the layer to the membrane is not particularly limited, and may be realized by any method customary to a person skilled in the art. For instance, the layer may be provided by applying, such as pipetting, an aqueous solution comprising a suitable polymer, a pH buffering compound and optionally a surfactant onto a membrane of the sensor. It is also possible to dip the sensor membrane into an aqueous solution comprising a suitable polymer, a pH buffering compound and optionally a surfactant.

In another aspect, the present disclosure relates to the use of a water-soluble (protective) layer having pH buffering properties for protecting a sensor (arrangement) for determining the concentration of an acidic or basic compound from ingress (entry) of an acidic or basic gas during non-use (e.g. storage, in particular for the time between manufacture and use) of the sensor.

The water-soluble layer having pH buffering properties may in particular comprise a polymer, a pH buffering compound and optionally a surfactant, as exemplified above in connection with the sensor.

In the context of the present application, the expression "for protecting a sensor . . . from ingress of an acidic or basic gas" may particularly denote that the effect on the sensing properties caused by the ingress or entry of an acidic or basic gas into the sensor is reduced by at least 30%, in particular by at least 50%, in particular by at least 70%, compared to a sensor without having a water-soluble protective layer with pH buffering properties.

The present disclosure is further described by the following figures and examples, which are solely for the purpose of illustrating specific embodiments, and are not construed as limiting the scope of the disclosure in any way. The illustrations in the drawings are schematic. In different drawings, similar or identical elements are provided with the same reference signs.

FIG. 1 schematically illustrates a sensor 100 according to an embodiment. The sensor 100 comprises a pH indicator 10 provided on a carrier 50. The pH indicator 10 is contained in an inner buffer 20, which is, apart from that, filled with a buffer solution sensitive to acidic or basic compounds. The buffer solution may for instance contain a hydrogen carbonate. The inner buffer 20 is covered by a membrane 30 which separates the inner buffer 20 from the environment, for instance—when the sensor is in use—from a sample side. However, the sensor 100 as shown in FIG. 1 is currently in non-use and therefore the membrane 30 is covered by a water-soluble layer 40 having pH buffering properties. As a result, undesired ingress of an acidic or basic gas into the inner buffer 20 can be suppressed or prevented. The layer 40 comprises for instance a polymer, such as carboxymethyl cellulose or polyethylene glycol, and a pH buffering compound, such as a hydrogen carbonate.

Figure 2:
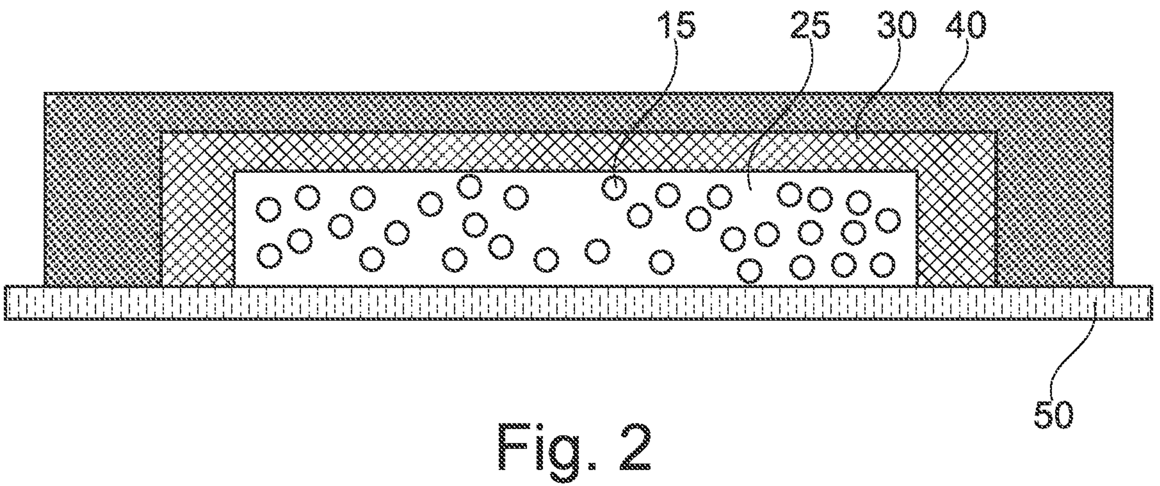
FIG. 2 schematically illustrates a sensor according to another embodiment.

FIG. 2 schematically illustrates a sensor 100 according to another embodiment. The sensor 100 as shown in FIG. 2 corresponds to the sensor 100 of FIG. 1 except for the inner buffer which is made of two components. Dispersed buffer beads 15 including a pH indicator in the embodiment are shown in FIG. 2. The dispersed buffer beads 15 may for instance contain a hydrogen carbonate as well as a pH indicator. They make up the internal electrolyte volume. They are embedded into a membrane material 25 filling up the rest of the inner buffer volume. The membrane material 25 has the same function as the membrane 30 covering the inner buffer volume and may even consist of the same material, but is usually applied in a different manufacturing step, together with the inner buffer beads 15, not with the membrane 30. Such "wet optodes" having dispersed buffer particles particularly suffer from storability problems caused by ingress of acidic or basic gases because the surface area is particularly large and the internal electrolyte volume and thus the buffer capacity is particularly small. However, by providing a layer 40 substantially covering the membrane 30 and comprising a water-soluble protective layer having pH buffering properties, these problems can at least be mitigated, if not resolved, even for such sensitive wet optodes.

Figure 3:
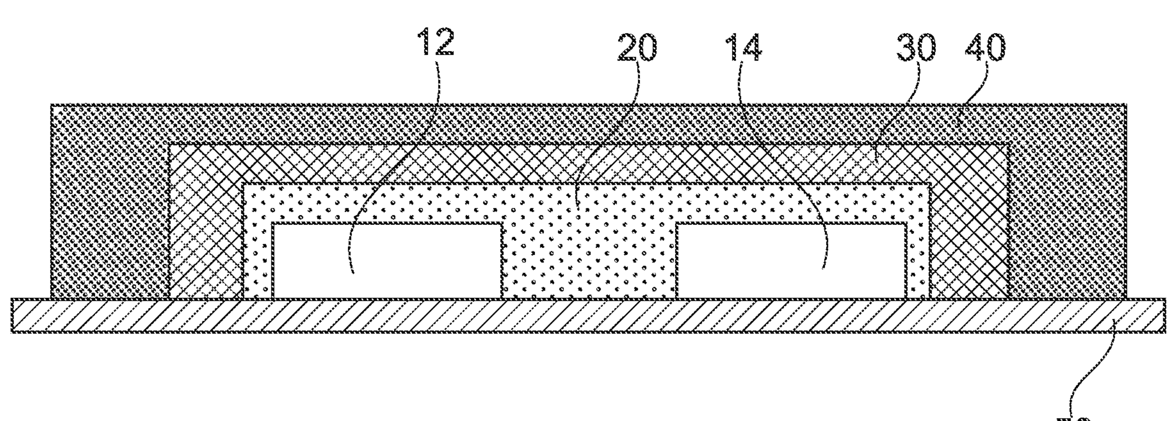
FIG. 3 schematically illustrates a sensor according to still another embodiment.

FIG. 3 schematically illustrates a sensor 100 according to still another embodiment. The sensor 100 as shown in FIG. 3 corresponds to the sensor 100 of FIG. 1 except for the pH indicator which is replaced by a pH electrode 12 combined with a reference electrode 14. Thus, the sensor 100 as shown in FIG. 3 represents a potentiometric Severinghaus type $CO_2$ sensor which may also be protected from ingress of undesired acidic or basic gases by a water-soluble layer 40 and having pH buffering properties.

EXAMPLES

Example 1

Preparation of Sensor Foil

A sensor layer was obtained by applying a mixture of particles according to the subject matter disclosed in EP 3789760 A1 to a transparent PET carrier having a thickness of 125 μm by knife coating with a coating thickness of 40 μm. A cover membrane was coated on top of said sensor layer, comprising a polymerizable silicone monomer solution mixed with white reflective particles and a crosslinker.

Example 2

Preparation of Protective Gel A

Sodium-Carboxymethylcellulose, low viscosity, Mw ~90 kg/mol (Sigma-Aldrich Inc.)

Sodium hydrogen carbonate (Merck)

Into a 100 ml laboratory bottle 2 g of Na-CMC was added either $NaHCO_3$ (168 mg) or HEPPS buffer (505 mg of HEPPS acid, 1.00 ml of 1 M sodium hydroxide solution) and dissolved in 48 ml of deionized water to yield a solution with 4% polymer content and 1 mM of buffer salt per g polymer.

Example 3

Testing of Storage Stability for Sensors with/without Protective Coating

The sensor foil from example 1 was placed on a piece of adhesive transfer tape sized smaller than the sensor foil to yield a three-layer sheet consisting of sensor foil, adhesive film, and release liner. A piece of 1×1 cm was cut from the three-layer sheet and a circular spot 2 mm in diameter was cut from it using a punch press, cutting through the sensor foil and the adhesive film, but not through the release liner. The outer part of sensor foil and adhesive layer were peeled off together, leaving behind a 2 mm sensor spot fixed by an equally sized piece of adhesive film on an otherwise bare release liner.

A small plate made of alumina (thickness 0.6 mm) with a hole 2.1 mm in diameter was pulled over the sensor spot on the release liner so that the spot was placed inside the hole. 10 μl of the solution prepared according to example 2 were pipetted onto the spot now integrated into the small plate using a piston pipette. That was achieved by adding solution onto the spot manually, covering the spot edge in a circulatory manner. In that way, the sensor spot was integrated into the aluminum oxide small plate, being covered by protective gel on its top and by the adhesive film on its bottom.

The small alumina plate holding the sensor spot was brought together with a silicone foil with an elongated hole in its middle and a polycarbonate workpiece to form a free inner space shaped 10 mm×1.6 mm×1.3 mm. The geometry of the free inner space was arranged for the silicone top layer of the sensor spot (covered with protective gel as described) to be essentially exposed to that free inner space. The "unit" obtained as just described, consisting of the free inner space and the components confining it, including the sensor spot, was open to the outer atmosphere through two approximately circular openings in the polycarbonate workpiece, having cross-sections of 0.3 $mm^2$ each. The unit was held together applying mechanical pressure by a screw clamp which was tightened manually. The unit was stored in air-tight pouches filled with a gas mixture containing 11% carbon dioxide, 18% oxygen and 71% nitrogen. It was stored at room temperature for a defined time.

Example 4

Effect of Protective Gel

A unit described in example 3 was disassembled after a given storage time, the sensor spot was removed from aluminum oxide small plate holding it and carefully detached from the substrates it had been glued onto using tweezers. It was affixed to the end of an optical fiber which was dipped into a solution containing physiological levels of $Na^+$, $K^+$ and $Cl^-$. The solution had been previously set to a $pCO_2$ of 40 mmHg applying a gas flow of 50 ml/min through it where the volume of the solution was 0.5 l. The sensor spot was conditioned in the solution for 2 hours and the sensor signal was interrogated by a suitable optics module. The optical fiber holding the sensor spot was dipped into similar solution with its $pCO_2$ set to 100 mmHg and the sensor signal was interrogated again after 10 min.

Typical results, each result is an average of at least 3 sensor spots in separate units, are shown in Table 1 below:

TABLE 1

| | w/o protective gel | | with protective gel comprising hydrogen carbonate | | with protective gel comprising HEPPS | |
|---|---|---|---|---|---|---|
| Storage time (weeks) | Phase shift at 40 mmHg | Phase shift at 100 mmHg | Phase shift at 40 mmHg | Phase shift at 100 mmHg | Phase shift at 40 mmHg | Phase shift at 100 mmHg |
| 0 | 24.4 | 32.8 | 24.4 | 32.8 | 24.4 | 32.8 |
| 5 | 25.1 | 36.1 | 19.8 | 28.6 | 20.9 | 30.7 |
| 16 | 33.8 | 44.5 | 20.9 | 30.2 | Not measured | |

The effect of protective gel becomes apparent by the lower increase in phase shift of both levels.

Example 5

Dissolution

Protective gel solution is spotted onto slides and dried at room temperature for more than 16 hours. When those slides are dipped into water a protective gels dissolve and are completely removed after a certain time, depending on material and molecular weight.

Protective gel A (4% CMC 90 kg/mol) is removed after 5 min and Protective Gel B (15% PEG 1 kg/mol) is removed after 1 min.

Example 6

Buffer Salt Concentrations in Different Polymers for Protective Layers

Protective gel solutions are prepared as described in example 2, with different types of polymers, types and amounts of buffer salts. 500 μl of each mixture are pipetted onto a silicone layer coated on a glass plate. The droplets/spots are left to dry for 48 h at 25° C., 50% RH and those where crystallization of buffer salt occurs are visually detected due to their opacity. Solubility for the buffer salt can be classified as "Clear">"Opaque">"White"

TABLE 2

| | Buffer Salt | | |
|---|---|---|---|
| Polymer | Type | Amount | Appearance |
| CMC, 90 kDa | NaHCO3 | 1 mM/g Polymer | Clear |
| CMC, 90 kDa | NaHCO3 | 2 mM/g Polymer | Opaque |
| CMC, 90 kDa | HEPPS | 1 mM/g Polymer | Clear |
| CMC, 90 kDa | HEPPS | 2 mM/g Polymer | Clear |
| PEG, 1 kDa | NaHCO3 | 0.5 mM/g Polymer | White |
| PEG, 1 kDa | HEPPS | 0.5 mM/g Polymer | White |
| PVP, 10 kDa | NaHCO3 | 1 mM/g Polymer | Opaque |
| PVP, 10 kDa | HEPPS | 2 mM/g Polymer | Clear |
| PVA, 10 kDa, 80% hydrolyzed | NaHCO3 | 1 mM/g Polymer | Opaque |
| PVA, 10 kDa, 80% hydrolyzed | HEPPS | 2 mM/g Polymer | Clear |

While the present disclosure has been described in detail by way of specific embodiments and examples, the disclosure is not limited thereto and various alterations and modifications are possible, without departing from the scope of the disclosure.

The invention claimed is:

1. A sensor for determining the concentration of an acidic or basic compound dissolved in water, wherein the determination is based on an ingress of gas or vapor of said compound, causing a change in pH value, within an inner buffer separated from a sample side by a membrane that is essentially permeable to gases and essentially impermeable to ions, characterized in that a layer is provided between the membrane and the sample side, wherein the layer substantially covers the membrane, wherein the layer is water-soluble and has pH buffering properties.

2. The sensor according to claim 1, wherein the layer comprises a polymer.

3. The sensor according to claim 2, wherein the polymer comprises at least one selected from the group consisting of carboxymethyl cellulose, polyethylene glycol, polyvinyl alcohol and polyvinylpyrrolidone.

4. The sensor according to claim 1, wherein the layer comprises a pH buffering compound.

5. The sensor according to claim 4, wherein the pH buffering compound comprises an inorganic compound.

6. The sensor according to claim 5, wherein the pH buffering compound comprises a hydrogen carbonate.

7. The sensor according to claim 4, wherein the pH buffering compound comprises an organic buffer salt.

8. The sensor according to claim 7, wherein the pH buffering compound comprises a mixture of 4-(2-Hydroxyethyl)-1-piperazinepropanesulfonic acid and its corresponding base.

9. The sensor according to claim 1, wherein the layer comprises a surfactant.

10. The sensor according to claim 9, wherein the layer comprises a nonionic surfactant.

11. The sensor according to claim 1, wherein the layer has a thickness in a range of from 50 nm to 5 mm.

12. The sensor according to claim 1, wherein the layer comprises a polymer in an amount of from 10 to 99.5% by weight and/or a pH buffering compound in an amount of from 0.01 to 75% by weight and optionally a surfactant in an amount of from 5 to 1000 ppm.

13. The sensor according to claim 1, wherein the membrane comprises silicone.

14. The sensor according to claim 1, wherein the sensor is configured for determining the concentration of dissolved carbon dioxide.

15. The sensor according to claim 1, wherein the inner buffer contains a pH buffering compound.

16. The sensor according to claim 15, wherein the pH buffering compound comprises a hydrogen carbonate, a phosphate or an organic buffer salt.

17. The sensor according to claim 16, wherein the hydrogen carbonate comprises sodium hydrogen carbonate and/or wherein the phosphate comprises disodium hydrogen phosphate or sodium dihydrogen phosphate.

18. The sensor according to claim 1, wherein the inner buffer contains a dispersion of a pH buffering compound in a liquid.

19. The sensor according to claim 1, wherein the sensor further comprises at least one of a pH indicator and a pH electrode.

20. A method of protecting a sensor for determining the concentration of an acidic or basic compound from ingress of an acidic or basic gas during non-use of the sensor, wherein the determination is based on an ingress of gas or vapor of said compound, causing a change in pH value, within an inner buffer separated from a sample side by a membrane that is essentially permeable to gases and essentially impermeable to ions, the method comprising:

providing a layer between the membrane and the sample side, wherein the layer substantially covers the membrane, wherein the layer is water-soluble and has pH buffering properties.

* * * * *